United States Patent
Wang et al.

(10) Patent No.: US 8,697,176 B2
(45) Date of Patent: Apr. 15, 2014

(54) METHOD OF CHANGING TRANSLUCENT PROPERTIES OF ZIRCONIA DENTAL MATERIALS

(75) Inventors: Hongjuan Wang, Benxi (CN); Qingyun Yan, Benxi (CN); Lingling He, Benxi (CN); Yanchun Zheng, Benxi (CN)

(73) Assignee: Liaoning Upcera Co., Ltd., Benxi, Liaoning (CN)

( * ) Notice: Subject to any disclaimer, the term of this patent is extended or adjusted under 35 U.S.C. 154(b) by 0 days.

(21) Appl. No.: 13/703,610

(22) PCT Filed: Nov. 21, 2011

(86) PCT No.: PCT/CN2011/001934
§ 371 (c)(1),
(2), (4) Date: Jan. 11, 2013

(87) PCT Pub. No.: WO2013/003990
PCT Pub. Date: Jan. 10, 2013

(65) Prior Publication Data
US 2013/0115365 A1    May 9, 2013

(30) Foreign Application Priority Data
Jul. 4, 2011   (CN) .......................... 2011 1 0183991

(51) Int. Cl.
*A61C 13/00*    (2006.01)
*B05D 3/08*    (2006.01)

(52) U.S. Cl.
USPC ......... 427/2.29; 427/2.1; 427/372.2; 501/152

(58) Field of Classification Search
USPC ................. 501/152; 427/2.27, 2.29
See application file for complete search history.

(56) References Cited

U.S. PATENT DOCUMENTS

| | | | | |
|---|---|---|---|---|
| 4,421,671 A | * | 12/1983 | Cusano et al. | 252/301.4 F |
| 7,608,553 B2 | * | 10/2009 | Fujita et al. | 501/152 |
| 2008/0241551 A1 | * | 10/2008 | Zhang et al. | 428/428 |
| 2010/0041542 A1 | * | 2/2010 | Rolf et al. | 501/104 |
| 2011/0318582 A1 | | 12/2011 | Ditttman et al. | |

FOREIGN PATENT DOCUMENTS

| | | |
|---|---|---|
| CN | 1810717 A | 8/2006 |
| CN | 101265088 A | 9/2008 |
| CN | 102028624 A | 4/2011 |
| JP | 2001-181031 A | 7/2001 |
| WO | WO 02074714 A1 * | 9/2002 |

OTHER PUBLICATIONS

International Search Report for patent application PCT/CN2011/001934 mailed on Apr. 12, 2012.

* cited by examiner

*Primary Examiner* — Cachet Sellman
(74) *Attorney, Agent, or Firm* — Kilpatrick Townsend & Stockton LLP

(57) ABSTRACT

The present invention relates to a method for changing translucency of zirconia dental materials through applying an yttrium or ytterbium salt solution onto a pre-sintered zirconia material by dipping or brush-coating. Accordingly, the need of young patient in relation to the translucent requirement for incisal portion of anterior teeth is met in which the translucent level from the crown neck to the incisal portion is gradually changed in a natural manner, similar to natural teeth. A color gradient effect of the crown is produced through dipping in or brush-coating with yttrium or ytterbium salt solution. Moreover, the present invention involves simple operating steps and low cost while providing high consistency in quality.

14 Claims, No Drawings

METHOD OF CHANGING TRANSLUCENT PROPERTIES OF ZIRCONIA DENTAL MATERIALS

TECHNICAL FIELD

The present invention relates to a method of changing properties of zirconia material, and more particularly to a method of changing the translucent property of zirconia dental material.

BACKGROUND

Yttria-stabilized zirconia tetragonal ceramics have good biocompatibility and excellent mechanical properties. In particular, They have much higher fracture toughness compared to alumina ceramics. Since the 1990s, zirconia ceramics have been used as crown materials in dental fixed restoration. However, because of their poor light-transmission, zirconia ceramics are required to be veneered onto the crown during post-processing when restoration of anterior teeth for young patients is performed for aesthetic purpose so as to mimic the appearance of natural teeth. As a result, the abutment preparation space requirement is increased. In addition, since the thermal expansion coefficient difference between zirconia and the ceramic veneer is relatively large while the zirconia and the ceramic veneer do not have good chemical bonding, the bond strength between the ceramic veneer and the zirconia is poor and thus the ceramic veneer may peel off or break easily. It is indicated by the clinical study of zirconia all-ceramic teeth that the failure rate of zirconia-based all-ceramic teeth is above 10% after a use period of 5 years. In order to solve the problems of veneer breaking and large amount of ready-for-use dental articles, a full zirconia restoration with higher translucency and without any ceramic veneer is put in use. However, this restoration has a single light-transmission, thus it is difficult to mimic the appearance of natural teeth regarding its translucent end and thus is aesthetically poor.

SUMMARY OF THE PRESENT INVENTION

An object of the present invention is to solve the above identified problems in the prior art and provides a method for changing a translucency of dental zirconia material. Thus the present invention solves the problem that the translucency of dental zirconia material in conventional technology can not meet the need of young patients in relation to the translucent requirement of incisal portion of anterior teeth. In addition, the present invention is advantageous in low-cost and quality consistency.

The technical solution of the present invention includes the following steps:

Preparation: preparing a solution with a concentration of 10~73 wt % of soluble yttrium salt in water or alcohol-water, Dipping I: dipping a pre-sintered zirconia in the above solution for 0.5~30 minutes, Drying: drying the pre-sintered zirconia as dipped above;

Sintering: sintering the dried pre-sintered zirconia at 1400~1600° C. for 2 hours in a high temperature box resistance furnace, and obtaining a zirconia material with gradual translucency or with high translucency in the whole body.

A dipping step II may exist between the drying step and the sintering step, i.e dipping in the soluble yttrium salt solution for 2~10 times.

The dipping steps I and II can also be substituted by brush-coating the pre-sintered zirconia with the yttrium salt solution or by dipping in and brush-coating with the yttrium salt solution.

A ytterbium solution can be used in place of said yttrium solution.

The principle of the present invention is as follows:

3Y-TZP is a tetragonal phase which exists phase transformation toughening and has a strength above 1000 mPa. However, it has a relatively low translucency which cannot meet the aesthetic need for anterior teeth in dental restoration. 8Y-FSZ is a cubic phase which is isotropic and translucent or transparent material can be obtained to meet the needs of young patient in relation to the translucent requirement for incisal portion of anterior teeth. However, because 8Y-FSZ does not have phase transformation toughening, its strength is only about 200 MPa. The content of Y is increased by dipping in and brush-coating with a yttrium or ytterbium salt solution, and a mixture material comprising tetragonal and cubic phases with high strength and high translucency is obtained, thereby the need of young patient in relation to the translucent requirement for incisal portion of anterior teeth is met. In addition, because the translucent requirement is met, the ceramic veneer is not needed, thereby the peeling off or breaking of ceramic veneer, which is caused by the thermal expansion coefficient difference between the zirconia material and the ceramic veneer, is avoided.

The advantageous effect of the present invention is described as follows:

By dipping in or brush-coating the zirconia material with a yttrium or ytterbium solution, the need of young patient in relation to the translucent requirement for incisal portion of anterior teeth is met in which the translucent level from the crown neck to the incisal portion is gradually changed in a natural manner, similar to the natural teeth. In addition, a color gradient effect can not be obtained for the crown prepared by adding coloring agents in zirconia powder or by using dyeing solution for dipping and dyeing the crown, while the dipping in or brush-coating the zirconia material with a yttrium or ytterbium solution can produce a color gradient effect of the crown. Moreover, the present invention involves simple operating steps and low cost while providing high consistency in quality.

DETAILED DESCRIPTION OF THE PREFERRED EMBODIMENT

The present invention is described in detail by combining with the following examples:

Example 1

First, an yttrium nitrate solution with a concentration of 10 wt % in polyethylene glycol-water is prepared. A portion of a pre-sintered zirconia is dipped in the yttrium nitrate solution for 15 minutes, then removed out from the solution and allowed drying in air. Thereafter the pre-sintered zirconia is sintered in a high temperature box furnace at 1400~1600° C. for 2 hours and a final product with gradient translucency is obtained.

The above final product is tested as follows:

(1) Three-point flexural strength (for sampling, refer to the test of bond strength between zirconia and ceramic veneer)

Equipment: TH8201-S servo desktop universal material testing machine

Sample size: length greater than 20 mm, width 4.0 mm, thickness 1.2 mm, span 16 mm, loading speed 0.5 mm/min.

Test result: Three-point flexural strength is 1076 MPa.

(2) Reflectivity contrast

Sample thickness is 1.0 mm and test result is 0.71

Example 2

First, an yttrium nitrate solution in water with a concentration of 30 wt % is prepared. A portion of a pre-sintered zirconia is dipped in the yttrium nitrate solution for 30 minutes, then removed out from the solution and allowed drying in air. Finally, the pre-sintered zirconia is sintered in a high temperature box resistance furnace at 1400~1600° C. for 2 hours and a final product with gradient translucency is obtained.

The above final product is tested by the same method as described in Example 1.

Test result: Three-point flexural strength is 953 MPa and the reflectivity contrast is 0.70.

Example 3

First, an ytterbium nitrate solution with a concentration of 45 wt % in polyethylene glycol-water is prepared. A portion of a pre-sintered zirconia is dipped in the yttrium nitrate solution for 5 minutes, then removed out from the solution and allowed drying in air. Thereafter the air dried zirconia is brush-coated with the ytterbium solution, allowed drying in air and sintered in a high temperature box resistance furnace at 1400~1600° C. for 2 hours. A final product with gradient translucency is obtained.

The above final product is tested by the same method as described in example 1.

Test result: Three-point flexural strength is 904 MPa and the reflectivity contrast is 0.69.

Example 4

First, an yttrium nitrate solution with a concentration of 73 wt % in polyethylene glycol-water is prepared. Then a portion of a pre-sintered zirconia is dipped in the yttrium nitrate solution for 0.5 minutes, removed out from the solution and allowed drying in air. Finally, the pre-sintered zirconia is sintered in a high temperature box resistance furnace at 1400~1600° C. for 2 hours and a final product with gradient translucency is obtained.

The above final product is tested by the same method as described in Example 1.

Test result: Three-point flexural strength is 873 MPa and the reflectivity contrast is 0.71.

Example 5

First, an yttrium nitrate solution with a concentration of 60 wt % in glycerol-water is prepared. Then a pre-sintered zirconia is brush-coated with the yttrium nitrate solution, allowed drying in air, and sintered in a high temperature box resistance furnace at 1400~1600° C. for 2 hours. A final product with gradient translucency is obtained.

The above final product is tested by the same method as described in Example 1.

Test results: Three-point flexural strength is 898 MPa and the reflectivity contrast is 0.70.

Example 6

First, an yttrium nitrate solution with a concentration of 50 wt % in tetrahydrofurfuryl alcohol-water is prepared. A portion of a pre-sintered zirconia is dipped in the yttrium nitrate solution for 3 minutes, then removed out from the solution, and allowed drying in air. Then the pre-sintered zirconia is brush-coated with the yttrium nitrate solution, allowed drying in air, and sintered in a high temperature box resistance furnace at 1400~1600° C. for 2 hours. A final product with gradient translucency is obtained.

The above final product is tested by the same method as described in Example 1.

Test result: Three-point flexural strength is 920 MPa and the reflectivity contrast is 0.68.

Example 7

First, an ytterbium nitrate solution with a concentration of 10 wt % in polyethylene glycol-water is prepared. Then a portion of a pre-sintered zirconia is dipped in the yttrium nitrate solution for 10 minutes, removed out from the solution and allowed drying in air. The dipping process is repeated for 3 times. Finally the dipped pre-sintered zirconia is sintered in a high temperature box resistance furnace at 1400~1600° C. for 2 hours and a final product with gradient translucency is obtained.

The above final product is tested by the same method as described in Example 1.

Test results: Three-point flexural strength is 1042 MPa and the reflectivity contrast is 0.69.

Example 8

First, an yttrium nitrate solution with a concentration of 70 wt % in water and a ytterbium nitrate solution with a concentration of 50 wt % in water are prepared. Then a portion of a pre-sintered zirconia is dipped in the yttrium nitrate solution for 5 minutes, removed out and allowed drying in air, and then dipped in the ytterbium nitrate solution for 5 minutes, removed out and allowed drying in air. The resultant pre-sintered zirconia is sintered in a high temperature box resistance furnace at 1400~1600° C. for 2 hours and a final product with gradient translucency is obtained.

The above final product is tested by the same method as described in Example 1.

Test result: Three-point flexural strength is 862 MPa and the reflectivity contrast is 0.67.

Example 9

First, an ytterbium nitrate solution with a concentration of 73 wt % in polyethylene glycol-water is prepared. Then a pre-sintered zirconia is brush-coated with the ytterbium nitrate solution, removed out and allowed drying in air, and further brush-coated with the ytterbium nitrate solution twice, and finally sintered in a high temperature box resistance furnace at 1400~1600° C. for 2 hours. A final product with gradient translucency is obtained.

The above final product is tested by the same method as described in Example 1.

Test result: Three-point flexural strength is 843 MPa and the reflectivity contrast is 0.67.

Example 10

First, an ytterbium nitrate solution with a concentration of 10 wt % in polyethylene glycol 600-water is prepared. Then a portion of a pre-sintered zirconia is dipped in the ytterbium nitrate solution for 10 minutes, removed out and allowed drying in air. The dipping process is repeated 10 times. Finally, the resultant pre-sintered zirconia is sintered in a high temperature box resistance furnace at 1400~1600° C. for 2 hours and a final product with gradient translucency is obtained.

The above final product is tested by the same method as described in Example 1.

Test result: Three-point flexural strength is 905 MPa and the reflectivity contrast is 0.68.

One skilled in the art will understand that the protection scope of the present invention is based on the claims and not intended to be limited by the specific examples.

What is claimed is:

1. A method for changing a translucent property of zirconia dental materials, comprising:
    preparing an aqueous or an alcohol-water solution of a soluble yttrium salt or a soluble ytterbium salt at a concentration of 10 wt % to 73 wt %, based on the total weight of the solution;
    treating a pre-sintered zirconia material with the salt solution to provide a treated zirconia material;
    drying the treated zirconia material;
    sintering the dried and treated zirconia material at 1400° C. to 1600° C. to obtain a final product of zirconia material with gradient translucency or high translucency.

2. The method of claim 1, the concentration of the salt is 70 wt %.

3. The method of claim 1, wherein the solution is an alcohol-water solution and the alcohol is selected from glycerol, glycol, polyethylene glycol, and tetrahydrofurfuryl alcohol.

4. The method of claim 1, wherein treating is selected from dipping the pre-sintered zirconia material in the soluble salt solution for 0.5 minutes to 30 minutes, dipping the pre-sintered zirconia material with the salt solution 2 to 20 times, brush-coating the pre-sintered zirconia material with the salt solution, or a combination of any of the foregoing.

5. The method of claim 1, wherein treating comprises dipping the pre-sintered zirconia material in the soluble salt solution for 0.5 minutes to 30 minutes.

6. The method of claim 1, wherein treating comprises brush-coating the zirconia material with the salt solution.

7. The method of claim 1, comprising, after drying the treated zirconia material, treating the dried and treated zirconia material with the salt solution.

8. The method of claim 7, wherein treating is selected from dipping the pre-sintered zirconia material in the soluble salt solution for 0.5 minutes to 30 minutes, dipping the pre-sintered zirconia material with the salt solution 2 to 20 times, brush-coating the zirconia material with the salt solution, or a combination of any of the foregoing.

9. The method of claim 7, wherein treating comprises dipping the pre-sintered zirconia material with the salt solution 2 to 20 times.

10. The method of claim 7, wherein treating comprises brush-coating the zirconia material with the salt solution.

11. The method of claim 1, wherein the solution is an yttrium salt solution.

12. The method of claim 1, wherein the solution is an ytterbium salt solution.

13. The method of claim 7, wherein the final product is characterized by a reflectivity contrast from 0.67 to 0.71.

14. The method of claim 1, wherein the final product is characterized by a three-point flexural strength from 843 MPa to 1076 MPa.

* * * * *